United States Patent [19]

Lenormand et al.

[11] Patent Number: 5,679,885
[45] Date of Patent: Oct. 21, 1997

[54] PROCESS AND DEVICE FOR MEASURING PHYSICAL PARAMETERS OF POROUS FLUID WET SAMPLES

[75] Inventors: Roland Lenormand, Rueil-Malmaison; Annick Eisenzimmer, Maule; Gabriel Ringot, Courbevoie, all of France

[73] Assignee: Institut Francais du Petrole, Rueil Malmaison, France

[21] Appl. No.: 668,371

[22] Filed: Jun. 18, 1996

Related U.S. Application Data

[63] Continuation of Ser. No. 282,239, Jul. 29, 1994, abandoned.

[30] Foreign Application Priority Data

Jul. 29, 1993 [FR] France ................... 93 09481

[51] Int. Cl.$^6$ ................... G01N 15/08
[52] U.S. Cl. ................... 73/38; 73/152.06; 73/597
[58] Field of Search ................... 73/38, 597, 152.05, 73/152.06, 152.07, 152.41

[56] References Cited

U.S. PATENT DOCUMENTS

| | | | |
|---|---|---|---|
| 4,506,542 | 3/1985 | Rose | 73/38 |
| 4,543,821 | 10/1985 | Davis | 73/153 |
| 4,868,751 | 9/1989 | Dogru | 73/38 |
| 4,926,128 | 5/1990 | Givens | 324/376 |
| 5,069,065 | 12/1991 | Sprunt et al. | 73/153 |
| 5,079,948 | 1/1992 | Collins et al. | 73/151 |
| 5,164,672 | 11/1992 | Gilliand et al. | 73/153 |
| 5,209,104 | 5/1993 | Collins et al. | 73/38 |
| 5,297,420 | 3/1994 | Gilliland | 73/38 |
| 5,345,819 | 9/1994 | Dearing, Jr. | 73/153 |

FOREIGN PATENT DOCUMENTS 0473500  3/1992  European Pat. Off. .

*Primary Examiner*—Christine K. Oda
*Attorney, Agent, or Firm*—Antonelli, Terry, Stout & Kraus, LLP.

[57] ABSTRACT

A process involves placing a solid sample imbibed or saturated with a first fluid (for example water) in a closed chamber; injecting, via pressure means, another liquid under pressure at a first end of the chamber to drain or expel the first liquid from the sample; and sweeping an opposite end of the chamber with a low pressure liquid, circulated by pumping means, which carries or discharges the drained first liquid outside the chamber. A device for conducting the process includes measuring means for determining the pressure and saturation variations of the sample at at least one point of the length of the sample in the chamber, the amount of fluid discharged from the chamber, and the electrical resistivity of the sample. A progressive variation of the flow of the liquid injected allows complete draining and imbibition cycles to be performed while setting up capillary pressure variation curves and calculating relative permeabilities, without touching the sample. Applications for the process include testing of geological samples, as well as building materials used in the building industry.

16 Claims, 2 Drawing Sheets

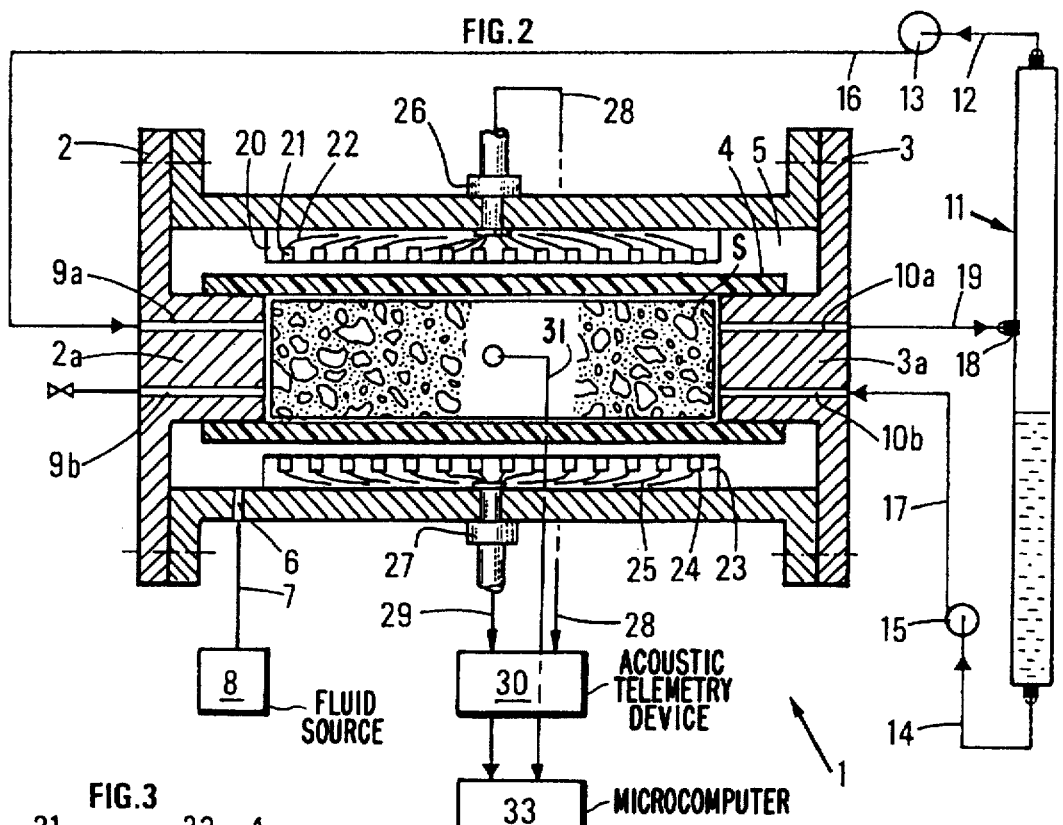
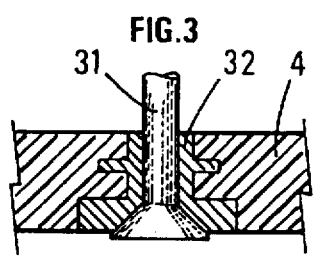
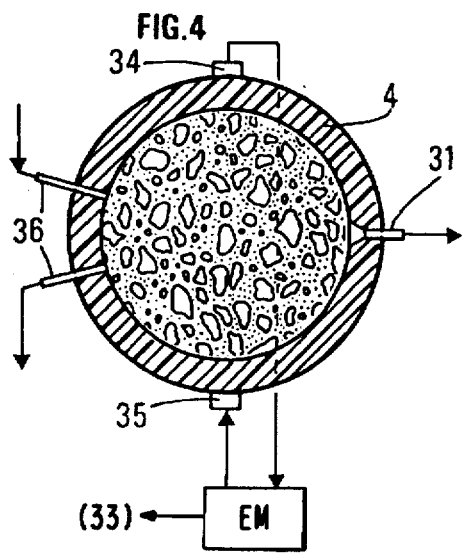
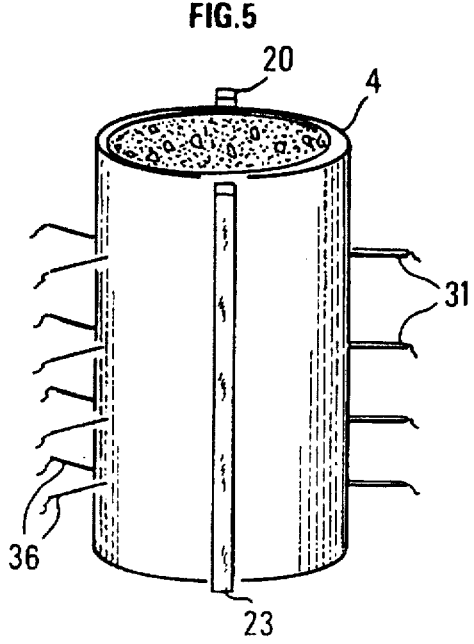

PROCESS AND DEVICE FOR MEASURING PHYSICAL PARAMETERS OF POROUS FLUID WET SAMPLES

This application is a Continuation application of application Ser. No. 282,239, filed Jul. 29, 1994, abandoned.

FIELD OF THE INVENTION

The present invention relates to a process and to a device for achieving, on a porous sample, successive draining and imbibition cycles so as to determine physical parameters of this sample.

The process and the device according to the invention are suitable for testing geological samples and for determining various parameters, such as the capillary pressure of rocks in draining or imbibition phases, their wettability indices, their relative permeabilities, their resistivity indices, etc.

The process and the device may notably be applied in the petroleum field for testing samples, e.g., rocks which have been taken in formations containing or likely to contain petroleum effluents.

It is important to determine the wettability of rocks with respect to the water and to the oil which may be contained therein. To that effect, the rock has to be subjected to a draining process, i.e. a displacement of the fluids intended to decrease the water saturation, followed by an imbibition, this term referring to a displacement of the fluids allowing the water saturation (Sw) of the rock to be increased. The capillary pressure at a point is defined as the difference Pc at equilibrium between the pressure P(oil) of the oil and the pressure P(water) of the water. This parameter is significant only if the two fluids are in the continuous phase in the porous medium. For a water wet medium, only the positive values are significant. On the other hand, when the medium has a mixed wettability, the fluids may remain in the continuous phase for positive as well as for negative capillary pressures (Pc).

For an application of this type, a complete cycle of measurement of the capillary pressure must thus comprise (FIG. 1):

a) a positive primary draining of an initially 100% water-saturated sample (curve C1),
b) a positive imbibition (curve C2),
c) a negative imbibition (curve C3),
d) a negative draining (curve C4), and
e) a positive secondary draining (curve C5).

Curves C2' and C3', respectively, correspond to a spontaneous imbibition and a negative primary imbibition.

Knowledge of various parameters and notably of the wettability of rocks is useful especially when an enhanced recovery of a formation has to be performed by draining the effluents contained therein through an injection of a fluid under pressure, and when the most suitable fluid (water or gas) for displacing the effluents is to be determined through preliminary tests.

The invention may also be applied to the civil engineering field for the hydrology of grounds intended to assess the degree of pollution thereof, or to the building industry in order notably to decide water-repellent treatments for example.

BACKGROUND OF THE INVENTION

A method for measuring the capillary pressure prevailing in the pores of a porous rock containing two fluids in the continuous phase, known notably through patent U.S. Pat. No. 4,506,542, and called a "porous plate" method, mainly consists in placing the sample in an elongated cell ending, at the opposite two ends thereof, in capillary barriers permeable to a first one of these two fluids, in injecting this first fluid under pressure through the first membrane and in measuring the pressure difference between the injection pressure and the pressure of the fluid discharged at the other end. The pressures of the two fluids and the capillary pressure Pc are constant along the sample, and the saturation is assumed to be uniform. With this type of method, the draining phase period is rather long and relatively fragile membranes have to be used for implementing it.

It is also well-known to measure the capillary pressure of fluid-saturated rocks by subjecting them to a progressive speed centrifugation and by measuring the amount of fluid produced according to the speed. The liquid-saturated sample is placed in a chamber whose axis is oriented in the direction of the centrifugal force and another fluid is injected, which takes the place of the expelled fluid as it is expelled. During the reimbibition phase, the speed is decreased so as to study the reintegration of the initial fluid into the sample. The pressure field created by the centrifugation is expressed as a function of the density, the radius R and the angular speed w through the relation: $\frac{1}{2} w^2 \cdot (Rmax^2 - R^2)$, for each fluid. It is imposed that the pressure of the two fluids is the same when leaving the sample and that it cancels out thereat. With this type of method, local saturations are calculated by an inversion program from the total amount of water expelled from the sample. This method is implemented for example in patent applications FR-A-2,666,147 and EN.92/15,215 filed by the applicant.

The previous methods are of the static type since, at equilibrium, there is no movement of fluids inside the sample.

According to another method called a "dynamic" method, a sample is placed in an elongated chamber ending, at the two ends thereof, in water-permeable membranes. At a first end, oil under pressure is injected directly into the chamber. Water is also injected, but this injection is performed through the membrane and at a lower pressure. At the opposite end, the oil is directly discharged while the water flows out through the end membrane. By adjusting the oil and water injection rates, the same capillary pressure can be obtained at the inlet and at the oulet of the chamber, which leads to a uniform saturation which may be deduced from the fluids balance. The capillary pressure is obtained for example by measuring the difference between the pressures of the oil and of the water at the chamber outlet.

Such a method is notably described by Brown H. W. in "Capillary Pressure Investigations" Petroleum Transaction AIME, Vol. 192, 1951.

SUMMARY OF THE INVENTION

The process according to the invention allows successive draining and imbibition phases to be performed on a porous solid sample wettable by at least a first fluid, so as to determine physical parameters (notably petrophysical parameters: capillary pressures, water saturation (Sw), etc). It comprises placing the sample into an elongated chamber provided with measuring means, and injecting a second fluid under pressure at a first end of the chamber, so as to expel a first fluid out of the porous sample and flowing out of the chamber the first fluid coming from the sample said process also comprising:

circulating a fluid at a set constant pressure at the end of the chamber opposite the first end, measuring in at least one place along the chamber the saturation of the sample and the pressure prevailing in the sample, and determining physical parameters of the sample.

The saturation variation of the sample is determined by measuring for example the variations of the velocity of ultrasounds through the sample or by means of a radiation emitted through the sample.

The variations of the electric conductivity of the sample may also be measured as said second fluid is injected.

According to an embodiment, the sample is placed in the chamber and successive operations of draining of the first fluid from the sample and of imbibition of the sample with the same first fluid are achieved, the second fluid expelled from the sample being discharged through a fluid current at a set pressure. It is thus possible to achieve positive or negative draining-imbibition operations successively, by inverting the part played by the two fluids concerned.

One of the fluids is for example water and the other fluid may be oil.

The implementing device allows successive draining and imbibition phases to be performed on a porous solid sample in order to determine physical parameters. It includes an elongated chamber intended to contain a sample imbibed with the first fluid, pressure means which may be connected to a first end of the chamber, to inject a second fluid under pressure so as to drain the first fluid from the sample, and means for measuring the pressure in at least one place of the sample. The device includes pumping means which may be connected to the end of the chamber opposite the first end, in order to establish a fluid circulation at a set pressure and to drive the fluids expelled from the sample out of the chamber, means for measuring the amount of first fluid discharged from the chamber and means for determining the fluid saturation of the sample.

The device may include means for imposing a static pressure on the sample, and connection means for connecting the pressure means and the pumping means alternately to an end of the chamber and to the opposite end thereof.

According to an embodiment, the saturation measuring means include acoustic telemetry means for determining the variations of the sound propagation time through the sample.

According to another embodiment, the saturation measuring means include means for determining the variations of the absorption coefficient of the sample with respect to a radiation emitted therethrough.

According to yet another embodiment, the saturation measuring means include means for measuring the electric conductivity of the sample.

According to an advantageous layout, saturation measuring means including several measuring units arranged along several cross-sections in various places along the sample are used. In this case, several pressure detectors may also be arranged in these sections.

The fluid circulating at the opposite end of the chamber is preferably identical to the first fluid coming from the sample.

Allowing the first fluid to take the same pressure as the circulating fluid saves from performing separate measurements of the pressure of the first and of the second fluids, and therefore spares the use of semipermeable membranes. The pressure of the first fluid is known here with precision and a source of possible errors is thus avoided.

The layout of the cell being symmetrical, it is not necessary to disassemble it prior to achieving a complete positive or negative draining-imbibition cycle with measurements of the capillary pressure in all the successive phases. The absence of semipermeable membranes prevents implementing difficulties in providing tightness or keeping the capillary continuity, etc.

Knowledge of the pressure of the sample in at least one place of its length and of the saturation index thereof allows determination of:

the capillary pressure, the wettability indices WI calculated from the areas delimited by the positive and negative capillary pressure curves, or variations of the saturation extreme points, and the relative permeabilities Kr.

The device also allowing electric measurements to be performed, it is thus possible to calculate the electric resistivity indices IR according to the saturation, for the various parts of the capillary pressure curve.

BRIEF DESCRIPTION OF THE DRAWINGS

Other features and advantages of the process and of the device according to the invention will be clear from reading the description hereafter of embodiments given by way of non limitative examples, with reference to the accompanying drawings in which:

FIG. 3 shows an embodiment detail allowing the setting of a pressure detector, FIG. 4 shows a layout, in a single transverse plane, of ultrasound, pressure and electric conductivity measuring means, FIG. 5 diagrammatically shows an array of measuring means distributed in several places along a sample set in the device according to the invention.

DESCRIPTION OF THE PREFERRED EMBODIMENTS

Figure 1:
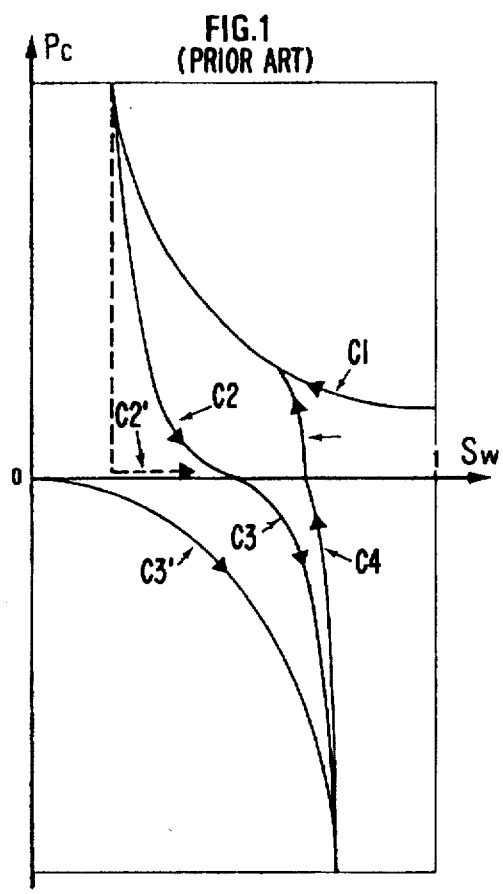
FIG. 1 shows prior art, for information only, the variations undergone by the capillary pressure in a sample during a complete draining-imbibition cycle, FIG. 2 diagrammatically shows a first embodiment of the device utilizing bars of ultrasound transducers for measuring the saturation.

The method according to the invention is of the semidynamic type and mainly consists in testing a sample during a draining phase as well as during an imbibition phase, by placing the sample in an elongated closed chamber and by injecting a first fluid under pressure at one of the ends of the chamber, while the opposite end is swept by means of a fluid current at a set lower pressure and at a low flow rate.

The method is implemented by means of a device including an elongated chamber or containment cell 1, for example cylindrical, which may be closed at the opposite two ends thereof by two removable covers 2, 3. Fastening and seal means (not shown) allow them to be fastened to the ends of the chamber. The sample S to be tested is placed inside a deformable housing 4 and the assembly is arranged in chamber 1. The two covers are provided, towards the inside of the chamber, with respectively a cylindrical bulge 2a, 3a having substantially the same diameter as that of the housing and adapted for engaging into the end parts thereof when covers 2, 3 are fastened to chamber 1. The annular space 5 around housing 4 communicates with a source of fluid under pressure 8 delivering fluid by means of an opening 6 provided in the outer wall of chamber 1 and of a line 7 connected to this opening. It may be a compressed gas bottle, a screw jack or a hydraulic pump. Application of this fluid allows the sample to be tested to be set under a determined pressure.

Outside chamber 1, a tube 11 closed at the two ends thereof is placed vertically. A line 12 which is connected to the inlet of a pump 13 is linked to the upper end of the tube. The lower end of tube 11 is connected through a line 14 to the inlet of a second pump 15.

Two channels 9a, 9b and 10a, 10b oriented parallel to the axis of the chamber are pierced through the cylindrical bulges, respectively 2a and 3a, of the two covers 2, 3. A line 16 connected to the outlet of the first pump 13 is linked to the channel 9a of cover 2 for example. A line 17 linked to the outlet of the second pump 15 is connected to channel 10b. Tube 11 is also provided with an intermediate radial opening 18 which is connected through a line 19 to the channel 10a in cover 3.

Tube 11 is for example transparent and graduated so that the level variations between the two fluids may be expressed in volumes of fluid expelled.

According to a first embodiment, means for detecting in at least one place of the length of sample S, and preferably in several places along its length, the variations of the saturation thereof are arranged inside chamber 1, outside housing 4. Ultrasound measuring means similar to those described in patent application EN.92/15,215 cited above are, for example, used.

A first bar 20, along which a row of piezoelectric pellets 21 associated each with electric wires 22 is fastened, is arranged along a first generating line of housing 4. Another bar 23, along which another row of piezoelectric pellets 24 also associated with conducting wires 25 is fastened, is arranged on the other side of the sample and in the same radial plane as the first bar 20. The electric wires 22 and 25 are respectively linked to two electric connectors 26, 27 running through the wall of chamber 1. Two cables 28, 29 connected to an acoustic telemetry device 30 of a known type are respectively linked to these two connectors. Device 30 periodically applies impulse signals to the pellets of bar 20, it receives the signals picked up respectively by the pellets of the opposite bar 23 and it determines, for each transreceiver couple, the propagation time (or flight time) of the impulses through the sample.

Calibrations achieved previously on a test sample or even during the measurings on the sample to be tested allow to establish a curve (FIG. 6) linking, for example, the oil saturation index So of a sample to the variation of the flight time Y of the ultrasounds passing therethrough (series of points C1 during the drainage and series of points C2 during the imbibition).

This method of measurement with ultrasounds is advantageous because of the relatively low cost and of the rate of response thereof. Besides, it is particularly well-suited for sample tests under pressure.

At least one pressure detector 31 is set inside housing 4 to measure the local pressure in a determined place of the length of the sample, preferably in the same transverse plane as one of the couples of piezoelectric pellets 21, 24. Detector 31 is placed for example in a metallic insert 32 running through the wall of the supple housing 4 (FIG. 3) and the associated electric conductors are connected externally to a data processing device 33 consisting for example of a programmed microcomputer. This microcomputer 33 also receives the flight time measurements achieved by the telemetry device 30.

Consider the case of an initially water-saturated sample for example, which is placed in chamber 1 and set under pressure by injecting fluid into the annular space 5 around housing 4. Oil under pressure is injected by means of pump 13 through channel 9a, at a set flow rate, at a first end of the sample. A water circulation with a constant low pressure (the atmospheric pressure for example or a set pressure imposed by a fluid tank at a reference pressure) and with a low flow rate is established at the opposite end. This water is recovered at the base of tube 11. The water is injected through pump 15 into channel 10b, and flows out through channel 10a while carrying along the fluids (water and oil) as they are expelled from sample S. Continuity is thus provided every minute between the circulating fluid and the water expelled from the sample. The mixture of fluids driven back into tube 1 through line 19 divides and the water flows back towards the lower part.

A first value is imposed on the oil flow. The fluids move inside the sample until an equilibrium is reached where the saturations and the pressures stabilize. The expulsion of water stops. There is a pressure gradient along the sample concerning P(oil). On the other hand, the pressure of the water P(water) is uniform at any point of the sample and equal to the pressure of the water circulating in circuit 17, 19. The equilibrium is achieved through the variation of the saturation which generates a capillary pressure gradient.

Figure 6:
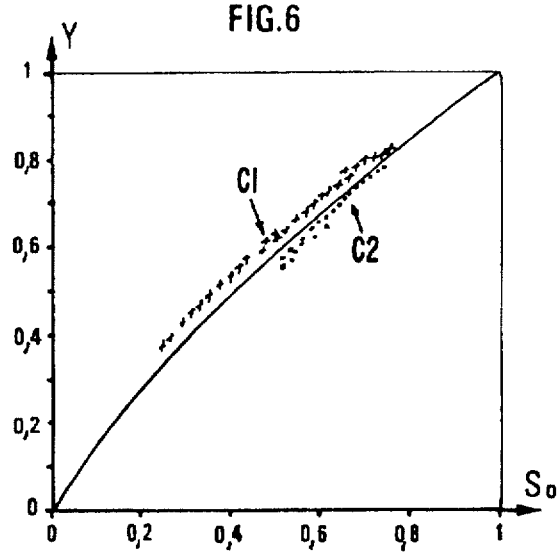
FIG. 6 shows a calibration curve of the ultrasound transducers allowing their propagation time interval or "flight time" Y to be linked to the oil saturation So of the sample for example.

The flight time of the ultrasounds is then measured (FIG. 2) by operating successively the couples of transmitters and receivers 21, 24 distributed along the sample. The distribution or profile of the oil saturation along the sample is determined with reference to the calibration curve established previously (FIG. 6). The local pressure P(oil) in the oil is also measured by means of detector 31 and the local capillary pressure $P_c$=P(oil)–P(water) is deduced therefrom. The volume of water expelled from the sample is also determined by measuring the variation of the interface position between the water and the oil in tube 11.

The oil flow rate is thereafter progressively increased by adjusting pump 13 and the previous measurements of the flight time, which are expressed in a distribution of the saturation values, are repeated, the local capillary pressure and the volume of water expelled are determined. The whole of the measurements achieved allows curve portion C1 to be established (FIG. 1). A stepwise decrease in the oil flow rate allows a progressive reimbibition as shown by the curve portion C2 of the curve.

Because of its symmetrical configuration, the device also allows the modes where the capillary pressure Pc is negative to be studied when the previous operations are completed. The previous sweeping of the end of the sample by means of a low-pressure water current circulating between channels 10a, 10b is, in this case, replaced by a sweeping using low-pressure oil circulating between channels 9a and 9b, also taken from tube 11, and by an application of water under pressure through channel 10b for example.

Figure 7:
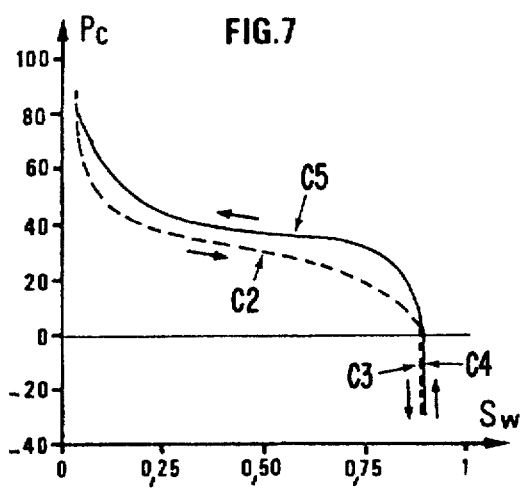
FIGS. 7 and 8 show, by way of example, how the capillary pressure Pc varies according to the water saturation Sw, for two samples respectively wettable with water and oil as obtained by use of the device of the invention.
Figure 8:
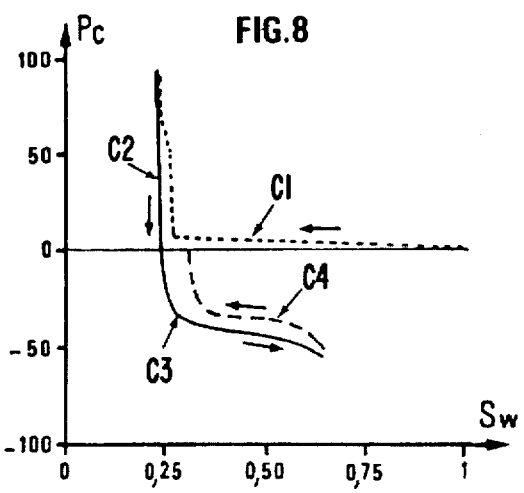

The measurements which are achieved with this symmetrical configuration allow curve portions C3 to be plotted by increasing and C4 by decreasing this flow rate (FIGS. 7, 8). The curve portion C5 is obtained like portion 1 by injecting oil and by sweeping the expelled fluid with water.

According to a variant of the previous embodiment, the saturation measurements may be obtained by replacing the previous ultrasonic transducer bars by a known device for transmitting and receiving an electromagnetic radiation (rays or X rays, etc) for example, including (FIG. 4) at least one wave transmitter 34 and at least one wave receiver 35 arranged so as to receive the waves which have crossed the sample. This transmission-reception couple is preferably arranged substantially in the same transverse plane as pressure detector 31 and it is connected to an absorption measuring device (not shown). Absorption measurements are performed at various successive stages of the injection phase and the successive saturation values may be deduced therefrom.

According to yet another variant of the previous embodiment, the saturation values are determined from electric resistivity measurements. This is obtained by means of electrodes 36 (FIG. 5) running through housing 4 and connected to a measuring device of a known type (not shown). At least one couple of electrodes 36 similarly arranged in the same transverse plane as pressure detector 31 is used.

An integrated petrophysics device has thus been achieved, with a body and a fluid distribution system such as that shown in FIG. 2. It is provided with two bars 20, 23 arranged outside the housing 4 containing the sample to be tested, with transducers 21, 24 distributed over the length thereof (FIG. 2). In each transverse plane containing a couple of transducers 21, 24, housing 4 is crossed by a couple of electrodes 36 and by an insert 32 for a pressure detector 31. With an acoustic telemeter such as telemeter 30 (FIG. 2), a conductivity measuring device (not shown) associated with electrodes 36 and the control microcomputer 33, a complete series of measurements is performed on a sample.

Curves relative to the variation of the capillary pressure Pc according to the saturation, such as those shown in FIG. 1, may for example be obtained by carrying out draining and imbibition cycles as described above.

Embodiments of the device including preferably means for measuring at several points along the sample the pressure and the saturation values have been described. This large number of measurements allows the accuracy of the results to be increased.

However, it is possible to limit oneself to local pressure and saturation measurements in a place of the length of the sample without departing from the scope of the invention.

We claim:

1. A device for performing, on a porous sample, successive draining and imbibition phases so as to determine physical parameters of the sample, said device comprising an elongated containment cell containing the sample imbibed with a first liquid, pressure means connected to a first end of the cell for injecting a second liquid under pressure into the cell and directly into the sample so as to drain or expel the first liquid from the sample, and means in the cell for measuring pressure in at least one portion of the sample and saturation measuring means for determining liquid saturation variation of the sample whereby said physical parameters are determined; said device also including pumping means and associated container means containing another portion of the first liquid connected to an end of said cell opposite the first end, for establishing a circulation of the first liquid at a set pressure at the end of the cell opposite the first end, which circulation acts to drive said first and said second liquids expelled or drained from the sample out of said cell into said container means, and means for measuring the amount of said first liquid discharged from said cell.

2. A device according to claim 1, further comprising means for imposing a static pressure on the sample within the cell.

3. A device according to any one of claims 1 or 2, further comprising connection means for connecting the pressure means and the pumping means alternately to the first end of the cell and to the end opposite the first end.

4. A device according to claim 1, wherein the saturation measuring means includes acoustic telemetry means for determining variations of sound propagation time through the sample.

5. A device according to claim 1, wherein the saturation measuring means include means for determining variations of absorption coefficient of the sample with respect to electromagnetic radiation emitted therethrough.

6. A device according to claim 1, wherein the saturation measuring means include several measuring units arranged along different cross-sections in various places of the cell along the sample.

7. A device according to claim 1, wherein the saturation measuring means include several saturation measuring units arranged along different cross-sections in various places of the cell along the sample.

8. A device according to claim 1, wherein the pressure means for injecting the second liquid is also connected to the container means, said container means comprising a tube arranged vertically outside of the cell, said pressure means comprising a first pump for introducing the second liquid taken from one end of the tube into the first end of the cell at a determined pressure and directly into the sample and said pumping means comprising a second pump for circulating the first liquid taken from an opposite end of the tube into the end of the cell opposite the first end to drive the first and second liquids drained from the sample from the cell into the tube, the first and second liquids taken from ends of the tube having different specific masses whereby these two liquids are separated within the tube.

9. A device according to claim 8, wherein the cell includes a rigid body, a supple chamber located inside the body and adapted to contain the sample, said chamber being delimited by a supple housing member and two rigid end pieces, each end piece having at least two channels passing therethrough, the saturation measuring being arranged in the body outside the chamber, at least one pressure detector placed in contact with the sample inside the chamber, liquid lines for connecting the channels in one of the end pieces to the pumping means and to the container means, and another liquid line for connecting a channel in the other end piece to the pressure means.

10. A device according to claim 1, further including a processing device connected to the pressure measuring means and to the saturation measuring means of the sample for determining said physical parameters.

11. A device according to claim 1, wherein the saturation measuring means include means for measuring the electric conductivity of the sample.

12. A process for performing, on a porous sample, successive draining and imbibition phases so as to determine physical parameters of the sample, comprising placing the porous sample containing a first liquid in an elongated chamber, injecting a second liquid under pressure into a first end of the chamber and directly into the sample to expel the first liquid out of the porous sample; measuring, in at least one place along the chamber, saturation variations of the sample; and measuring pressure prevailing in the sample, whereby physical parameters of the sample are determined, said process further comprising:

discharging the first liquid expelled from the sample out of the chamber by circulating another portion of the first liquid at a set constant pressure at an end of the chamber opposite the first end.

13. A process for performing, on a porous sample, successive draining and imbibition phases so as to determine physical parameters of the sample, comprising placing the porous sample containing a first liquid in an elongated chamber, injecting a second liquid under pressure into a first end of the chamber and directly into the porous sample, so as to expel the first liquid out of the porous sample, and measuring, in at least one place along the chamber, the pressure prevailing in the sample, said process further comprising:

measuring, in at least one other place along the chamber, variations of liquid saturation of the sample by measuring variations of ultrasound speed through the sample in the at least one other place, whereby physical parameters of the sample are determined, and discharging the first liquid expelled from the sample out of the chamber by circulating another portion of the first liquid at a set constant pressure at an end of the chamber opposite the first end.

14. A process according to claim 13, wherein after placing the sample in the chamber, successive operations of draining of the first liquid of the sample and of forced reimbibition of the sample with the same first liquid are effected, the second liquid expelled from the sample being then discharged through a liquid current caused by said liquid circulation at a set pressure.

15. A process according to claim 14, wherein displacement of the first liquid and injection of the second liquid are thereafter reversed.

16. A process according to claim 13, wherein one of the first and second liquid is water and the other liquid is oil.

* * * * *